United States Patent [19]

Warwick et al.

[11] Patent Number: 5,056,505
[45] Date of Patent: Oct. 15, 1991

[54] CHEST COMPRESSION APPARATUS

[75] Inventors: Warren J. Warwick, Minneapolis; Leland G. Hansen, St. Paul, both of Minn.

[73] Assignee: Regents of the University of Minnesota, Minneapolis, Minn.

[21] Appl. No.: 472,333

[22] Filed: Jan. 30, 1990

Related U.S. Application Data

[63] Continuation-in-part of Ser. No. 366,686, Jun. 12, 1989, abandoned, which is a continuation of Ser. No. 45,888, May 1, 1987, Pat. No. 4,838,263.

[51] Int. Cl.⁵ .............................................. A61H 31/02
[52] U.S. Cl. .................................... 128/30.2; 128/28; 128/24 R
[58] Field of Search ................. 128/28, 30, 30.2, 24 R; 137/625.21, 625.22

[56] References Cited

U.S. PATENT DOCUMENTS

| | | | |
|---|---|---|---|
| 3,507,297 | 4/1970 | Dann | 137/625.21 X |
| 4,577,626 | 3/1986 | Marukawa et al. | 137/625.21 X |
| 4,762,302 | 8/1988 | Bandou et al. | 137/625.21 X |
| 4,840,167 | 6/1989 | Olsson et al. | 128/30.2 X |
| 4,928,674 | 5/1990 | Halperin et al. | 128/30.2 |
| 4,930,498 | 6/1990 | Hayek | 137/625.21 X |

Primary Examiner—Robert Bahr
Assistant Examiner—L. C. M. Dvorak
Attorney, Agent, or Firm—Merchant, Gould, Smith, Edell, Welter & Schmidt

[57] ABSTRACT

Oscillatory chest compression apparatus to aid in loosening and eliminating mucus from the lungs of a cystic fibrosis patient. The apparatus includes a mechanism for applying pressurized air to a bladder covering the chest of a person and a mechanism for venting pressurized air from the bladder. In addition, the apparatus includes a mechanism for supplying the air to the bladder in a pattern of pulses having high rise times like square waves. The application of the pressurized pulses and the pulse rate is controllable by the patient.

4 Claims, 5 Drawing Sheets

CHEST COMPRESSION APPARATUS

This application is a continuation-in-part of application Ser. No. 07/366,686, filed Jun. 12, 1989, now abandoned, which is a continuation of application Ser. No. 07/045,888, filed May 1, 1987, now issued as U.S. Pat. No. 4,838,263.

FIELD OF THE INVENTION

The present invention relates generally to medical devices and, more specifically, to chest compression devices which aid in the loosening and elimination of mucus from the lungs of a person, particularly people affected by cystic fibrosis.

BACKGROUND OF THE INVENTION

Cystic fibrosis is a deadly hereditary disease. With one in 20 people carrying the recessive gene, conception of a child having cystic fibrosis results in approximately one in every 400 child-bearing marriages. No cure for the disease has been discovered. Cystic fibrosis affects the mucus secreting glands of the body so that there is an overproduction of mucus. The lungs are continuously filled with the excess mucus, and it must be removed daily to reduce the build-up and the risk of infection. Presently, treatment involves an aerosol therapy three or four times a day to obtain bronchial drainage and a daily physical pounding on the chest wall to loosen mucus for expectoration. Daily treatment can range from four to six hours plus and necessitates a respirator therapist or at least a trained individual to provide the pummeling of the chest.

The present invention rests on a premise derived from past research with dogs. Oscillating pressure aids mucus clearance in airways and concurrent vibrations decreases the viscosity of the mucus thereby enhancing motility. The research on dogs made use of a modified blood pressure cuff wrapped around the dog in the region of the rib cage. The air bladder in the cuff was pressurized by an oscillating pump.

The art in the area of mechanical vibrations to the body shows such things as inflatable jackets or garments to put on a person to aid in respiration, such as artificial respiration. U.S. Pat. No. 3,043,292, U.S. Pat. No. 2,354,397, U.S. Pat. No. 2,588,192 are representative. Additionally, a garment which provides oscillations for the purpose of massaging the body is shown in U.S. Pat. No. 3,310,050. The art, however, does not address the indicated cystic fibrosis treatment problem.

SUMMARY OF THE INVENTION

The present invention is directed to compression apparatus for the thoracic region of a person. The apparatus includes mechanism for applying a force to the thoracic region of the person. The force applying mechanism includes a bladder for receiving pressurized air. The apparatus further includes mechanism for supplying pressure pulses of the pressurized air to the bladder. The pulses supplied have a rise time at least twice as fast as the rise time of a sinusoidal pulse of equivalent amplitude frequency. Additionally, the apparatus includes mechanism for venting the pressurized air from the bladder.

In the preferred embodiment, a rotary valve determines the rate of air pulses entering the bladder from the pressure side and allows air to evacuate the bladder on the depressurizing side. A blower is used on the pressurizing side of the rotary valve. The valve advantageously provides a substantially square pulse. In this regard, the valve has a port leading from the blower to the bladder which has straight forward-most and rearward-most edges, while the rotary shutter of the valve has substantially parallel, straight leading and trailing edges. In that way, as the port is opened to provide communication between the blower and the bladder, the port is opened across a wide front thereby creating a fast rise time in the pressure pulse in the form of a substantially square wave. Although not necessary, the preferred embodiment also includes a control switch to function a solenoid valve on the pressurizing side of the rotary valve to stop pressurization during the inspiration portion of the patient's breathing cycle, depending on the desire of the patient.

In an alternative embodiment, a primary bellows is oscillated to provide air to the bladder adjacent to the chest of a person. In addition, the secondary bellows is oscillated to fill an air reservoir which can rapidly fill the bladder after it has been emptied during an inspiration.

The inventive apparatus is a pioneering solution to the treatment problem faced by people having cystic fibrosis. The advantages of the invention relate to benefits derived from a treatment program utilizing the present apparatus rather than a conventional treatment program. In this regard, a treatment program with the present apparatus provides a cystic fibrosis patient with independence in that the person can operate the machine alone. He/she is no longer required to schedule treatment with a trained individual. This results in increased psychological and physical freedom and self esteem. The person becomes flexible in his/her treatment and can add extra treatments if such would be beneficial as in the case of fighting a common cold. An additional benefit is the vast decrease in cost of treatment.

BRIEF DESCRIPTION OF THE DRAWINGS

The advantages and objectives of the present invention are explained with particularity hereinafter by referring to the drawings briefly described as follows.

DETAILED DESCRIPTION OF THE PREFERRED AND ALTERNATE EMBODIMENTS

Figure 1:
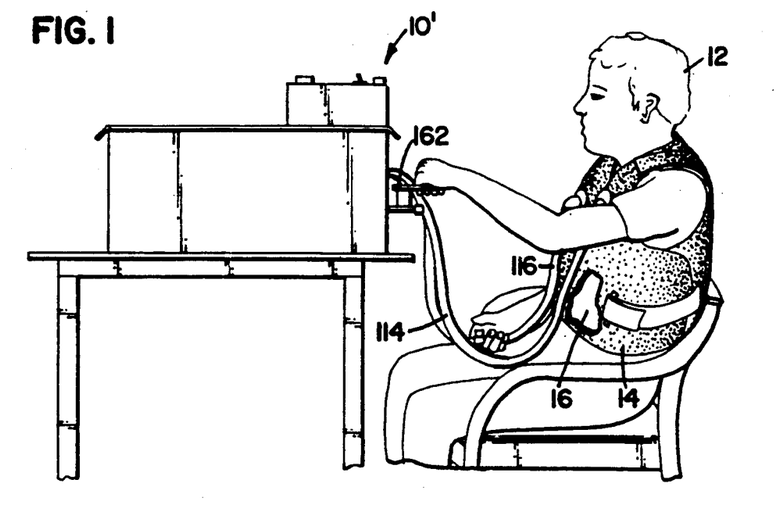
FIG. 1 is an illustration of a person operating the alternate embodiment apparatus in accordance with the present invention.
Figure 2:
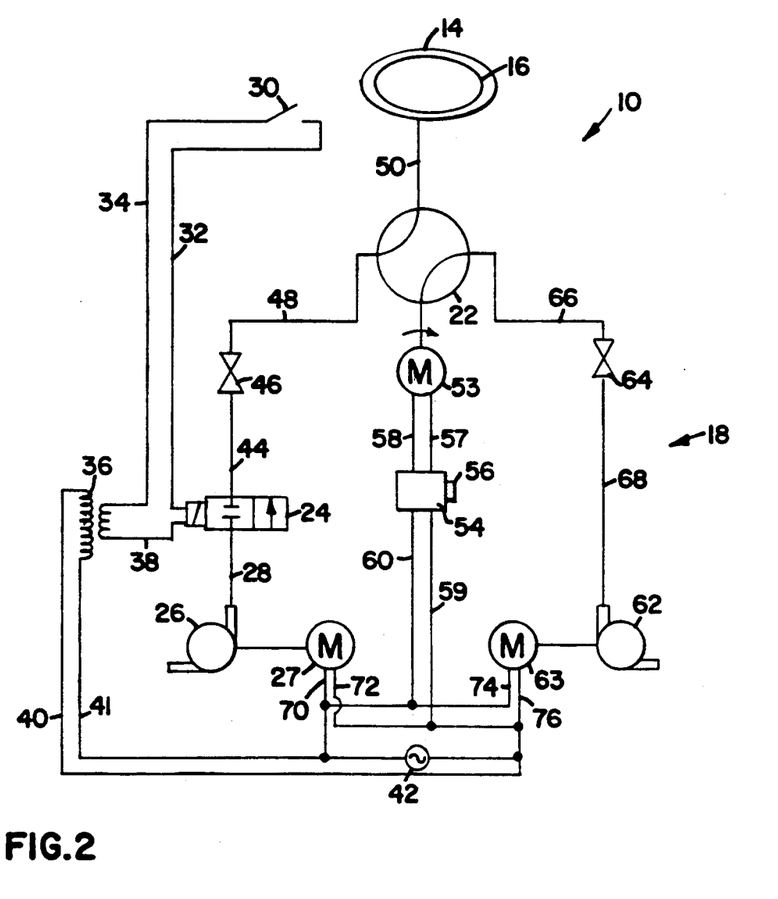
FIG. 2 is a schematic diagram of an apparatus in accordance with the preferred embodiment of the present invention.

Referring then to the drawings wherein like reference numerals designate identical or corresponding parts throughout the several views, and more particularly to FIG. 2, an apparatus in accordance with the present invention is designated generally by the numeral 10. With reference to FIG. 1, an alternate embodiment apparatus is designated generally by the numeral 10'. In FIG. 1, person 12 is shown wearing a shell 14 with an air vest or bladder 16 between the shell and his chest. A hose 114 connects the pulse pumping system 18 with vest bladder 16. Person 12 is shown with his left hand regulating switch 162 which controls the supply of air pulses to vest bladder 16, and with his right hand controlling the venting of vest bladder 16 by opening or closing the end of tube 116.

Embodiment 10 could be illustrated similarly to FIG. 1, except it is controllable with only one hand, as will become apparent. As shown in FIG. 2, the air pulse system 18 of apparatus 10 comprises a pair of high volume regenerative blowers 26 and 62 having output which is controlled by a large bore rotary valve 22. The pressure side blower 26 has been tested using a commercially available unit capable of producing a pressure of 43 inches of water at a volume of 53 cubic feet per minute. Blower 26 is driven by a motor 27. The test unit was driven by a one-half horse-power AC motor at 1725 rpm. The evacuation side blower 62 is driven by a motor 63. The test blower was capable of producing a pressure of 28.5 inches water at a volume capacity of 27 cubic feet per minute. The test blower was operated by a one-eighth horsepower AC motor at 1725 rpm. Preferably, the pressure side blower 26 is oversized relative to the evacuation side blower 62, as indicated with respect to the test units to accomplish fast reinflation of vest bladder 16 after it has been evacuated.

Alternate positive and negative pressures are applied to vest bladder 16 via a rotary valve 22. During the positive input pulse through valve 22 the negative pressure side of the system is closed. During the negative pressure pulse the positive pressure side of the system is closed. The rotary valve creates alternating positive and negative pressure pulses to vest bladder 16 and is driven by motor 53. During testing, a one-twentieth horsepower DC motor 53 controlled by a conventional DC controller 54 was used. An electronic tachometer with a magnetic pickup was used to monitor valve rotational speed. The blowers operated continuously, so that pulse speed was regulated by controller 54.

A solenoid valve 24 is located between the positive side blower 26 and the rotary valve 22. During testing, solenoid valve 24 had a 1.25 inch bore and was operated by 24 volt power. Valve 24 is normally closed and is controlled by a patient held hand switch 30. In the open position a positive 43 inches of water pressurized air flow is applied to rotary valve 22 which in turn allows the air in the form of a pressure pulse through to vest bladder 15. Since rotary valve 22 opens and closes air flow between positive side blower 26 and vest bladder 16, pulses are created. The pulsing rate is determined by the rotational speed of rotary valve 22 which in turn is determined by motor controller 54.

When solenoid valve 24 is in the closed position, no air flow from the positive side blower 26 passes to vest bladder 16. Rather, vest bladder 16 is evacuated by negative pressure side blower 62. Such evacuation reduces the efforts required by a patient during inhalation. Some patients may find a negative pressure is not needed to evacuate the vest for comfortable inhalation. For such patients, the vacuum or negative pressure blower 62 is optional.

A manual flow valve 46 is located between positive pressure blower 26 and vest bladder 16 to provide adjustment for regulating the flow volume or pulse strength to vest bladder 16. Likewise, a manual flow valve 64 is located between rotary valve 22 and negative side blower 62 to provide control relating to evacuation. That is, for some patients total evacuation of vest bladder 16 may be unnecessary or undesirable. Since rotary valve 22 rotates at a constant speed and since negative side blower 62 operates at a constant speed, when flow valve 64 is set to constrict the flow communication line between rotary valve 22 and blower 62, it will in effect reduce the volume of air which is evacuated during a revolution of rotary valve 22. Therefore, depending on how long the pressure side of apparatus 10 is closed, complete evacuation by the evacuation side may not occur.

With reference to FIG. 2, apparatus 10 is hereinafter described even more particularly. Pressure side blower 26 is in flow communication through hose 28 with normally closed, solenoid valve 24. It is understood that any reference to a hose could as well be a pipe or other mechanism for directing air from one point to another. Solenoid valve 24 is in flow communication with rotary valve 22 through a flow control valve 46, preferably manually operable, wherein hose 44 connects solenoid valve 24 with flow control valve 46 and hose 48 connects flow control valve 46 with rotary valve 22. One or more lines shown as hose 50 connect rotary valve 22 with vest bladder 16. On the negative pressure side, rotary valve 22 is in flow communication through flow control valve 64 with evacuation fan 62. Hose 66 connects rotary valve 22 with flow control valve 64, while hose 68 connects valve 64 with fan 62.

AC motor 27 drives pressurizing fan 26 and is connected via electrical lines 70 and 72 to electrical power source 42. AC motor 63 drives evacuation fan 62 and is connected via lines 74 and 76 to power source 42. DC motor 53 is connected via lines 57 and 58 with controller 54. Controller 54 includes a manual control 56 for varying speed of motor 53. Motor controller 54 receives power via lines 59 and 60 from source 42.

Solenoid valve 24 is connected through an isolation transformer 36 to power source 42. More particularly, solenoid valve 24 is connected to one side of transformer 36 via line 38 and to the other side of transformer 36 via lines 32 and 34 through patient control switch 30. The other side of transformer 36 is connected to power source 42 via lines 40 and 41.

A cystic fibrosis patient is generally weak and has a weak cough and cannot clear mucus from his/her lungs, sometimes hardly at all. A high frequency vibration aids in decreasing the viscosity of the mucus, freeing it from lung walls and thus making it much more likely that a weak cough will be able to clear mucus. As some mucus is cleared, the cough will likely strengthen thereby allowing more and more mucus to be cleared.

Figure 4:
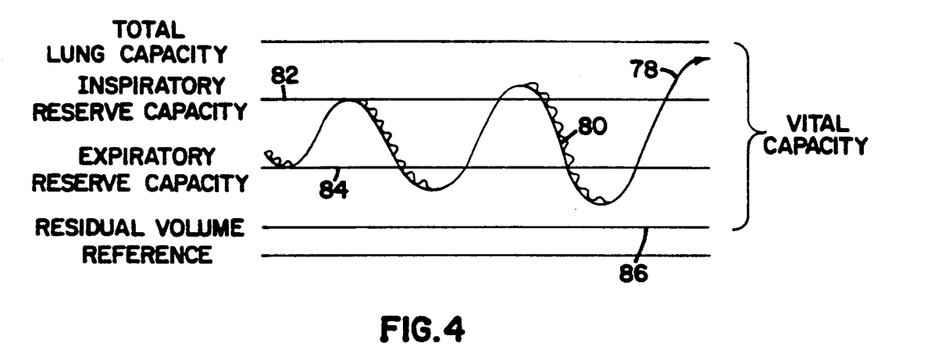
FIG. 4 is an illustration of pressure pulses superimposed on an oscillatory curve representing a patient's breathing cycle.

A more graphic representation is shown in FIG. 4. The lower frequency line 78 represents the breathing cycle of the patient. The higher frequency line superimposed on portions of the low frequency line represents the pulsing motion administered by vest bladder 16 to the patient's chest.

Initially, the patient breathes rather shallow and uses only a small percentage of his/her total lung capacity as represented by the region between the inspiratory reserve capacity line 82 and the expiratory reserve capacity line 84. As some mucus clears, the patient begins using a greater percentage of his/her lung capacity. A treatment goal is to get the patient breathing so deeply that he/she reduced his/her residual volume as represented by line 86, thereby increasing his/her vital capacity.

To use apparatus 10, first a vest bladder 16 and a shell 14 are custom made for the particular patient 12. The vest bladder 16 must cover the region of the chest which covers the lungs. The vest bladder has a single air chamber with at least one and preferably two air ports located near the upper portion of the chest. The vest, on a test model, was made of 15 mil polyurethane with hook and loop closures in front.

Shell 14 may be any one of several possible types. For example, the hard shell may be made from a polypropylene body cast to have split sides to allow for an easy fit. On the other hand, shell 14 may be made as a soft vest from a non-stretch cloth material. Or, shell 14 may be made of non-stretch cloth material, but made to have front and back panels forming pockets to receive rigid polypropylene plates. All shell types preferably include hook and loop closures.

After the patient has been fitted with a vest bladder 16 and shell 14 such that vest bladder conforms to the patient's chest snugly, but not tightly, hose 50 is connected thereto. The three motors 27, 53 and 63 are then turned on. Since solenoid valve 24 is normally closed, fan 26, although operating, is not yet pressurizing vest bladder 16. Evacuation fan 62, also now operating, is functioning to evacuate vest bladder 16. The patient then closes switch 30 which opens solenoid valve 24 and allows for pressurization of vest bladder 16 and does so with air pulses at a frequency set by control 56 of motor controller 54. If the volume of air from either the pressure side or the evacuation side of the system is too great or not enough, hand control valves 46 and 64 are appropriately functioned.

With the system operating, the patient must learn to control apparatus 10 in accordance with his/her breathing cycle. That is, switch 30 must be held down during expiration and released during inspiration so as to provide pulsing during expiration and evacuation during inspiration. The effect is shown graphically in FIG. 4 by the smooth line 78 directed toward inspiratory reserve capacity line 82 and the superimposed wave line 80 on line 78 directed toward expiratory reserve capacity line 84. The high frequency pulse rate appropriate for any particular patient is obtained by empirically measuring either the flow rate or the volume of air breathed by the patient at different frequencies and at different time durations of the treatment with apparatus 10. The present apparatus is particularly advantageous in this regard since the pulsing frequency can be tuned to a particular patient to optimize energy transmission to the lungs. Typically, the breathing cycle is a relatively low frequency and for a healthy person is commonly about 0.2 to 0.4 hertz. For a person having cystic fibrosis or other sickness, the breathing frequency may range up to one or two hertz. The high frequency pulsing is generally tuned between 10 to 30 hertz and could go as high as the 30 hertz rate for a small child. In any case, the low frequency breathing cycle will be below 5 hertz, while the high frequency pulsing cycle will be above 5 hertz.

After using briefly apparatus 10' described hereinafter and then after using more extensively apparatus 10 described hereinbefore, we determined that the pressure pulse wave form was an extremely important characteristic of the system. That is, quick impact is much more important than gradual compression. Hence, we realized the quick rise time of a pulse in a form of substantially a square wave is necessary. As a result of our testing, our preferred embodiment is essentially the system shown in FIG. 2 without exhaust blower 62 and flow valve 64. Also, we have found that a shell 14 is unnecessary.

In this regard, although not shown in the drawings in the detail described, the vest 16 in the preferred embodiment is tailored for each patient to cover the entire torso from over the shoulder to the iliac crest. The vest 16 is made of non-stretch vinyl coated polyester fabric 18 mil thick. Each vest 16 has two input ports located on each side of the upper front panels. The connect tubes are 1.85 cm internal-diameter, flanged vinyl elbows facing down to facilitate connecting by the patient. The front of the vest 16 is secured with hook and loop straps to assure a snug fit vest at total lung capacity along with quick release and closure. The straps overlap the left side of the vest 16 and are easily released by a small outward pull. The vest 16 has two anti-ride up loops located on the lower margin under each arm. These allow attachment of a loop strap on which the patient may sit during use when vest ride-up is a problem. The vest 16 is inflated over the entire thorax including air passages over the shoulders and under the arms. Construction of the vest 16 is accomplished using an industrial sewing machine and vinyl glue. All seams are double row stitched with heavy duty nylon thread. Input vinyl tubes are flanged inside the vest and sewn and glued in place. The input tubes 50 of the vest 16 are connected to the rotary valve 22 with 2.3 cm inside diameter and 2.6 cm outside diameter clear polyvinyl tubing. The vest 16 is not required to be air tight because a long time constant leak will not diminish pulse pressure in a high volume air stream.

The air pulse generator consists of a high volume regenerative blower 26 wherein output is controlled by a large bore rectangular port, rotary valve 22. The pressure blower 26 has a 1.5 cubic meters/min. capacity, capable of generating a maximum pressure of 130 mm Hg per sq. cm at 60 Hertz and operates off a ½ hp AC motor at 3450 RPM. Alternating positive and atmospheric pressures are applied to the vest 16 via the rotary valve 22. During inspiration, the atmospheric phase, the positive pressure side of the system can be blocked.

The rotary valve 22 which allows alternating positive and zero pressure, is driven by a 1/20 hp DC motor 53 controlled by a standard DC speed controller 54. Calibration of the speed controller 54 is done with a mechanical tachometer (not shown). The blower 26 operates continuously and pulse frequency is regulated by the rotary valve speed controller 54.

A 24 volt, 1.25 inch bore solenoid 24 is located between the positive pressure blower 26 and the rotary valve 22. This valve 24 is normally closed and is controlled through an isolation circuit by a patient held hand or foot dead mans switch 30. Should the patient drop the switch or fall, no pressure is applied to the vest 16 which then deflates through the rotary valve 22 and the constant vest leakage. In the open position, a positive 130 mm Hg pressure is applied to the rotary valve 22 which in turn allows pulses to reach the vest 16. In the closed position, no pressure is applied to the rotary valve 22 and the vest 16 empties through the atmospheric pressure side of the rotary valve 22. This reduces patient effort during inhalation. A manual flow control valve 46 is located between the positive pressure blower 26 and the rotary valve 22. This valve 46 can be adjusted to regulate the air flow (pulse strength) to the vest 16.

Pressure pulse wave forms produced by the rotary valve 22 at various frequencies were determined by placing a probe from a pressure transducer in the vest 16. The pressure transducer was calibrated using a mercurial sphygmomanometer. The transducer was connected to an oscilloscope where the wave forms were displayed and photographed.

Figure 8:
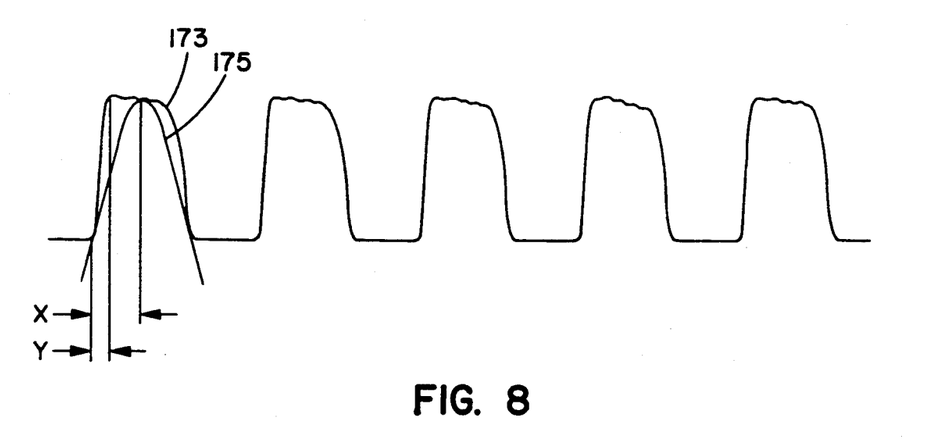
FIG. 8 is an illustration of a series of square wave pressure pulses appropriate with apparatus in accordance with the present invention as compared to a sine wave.

Using valve 22 described hereinafter, near square wave pulses as shown in FIG. 8 were produced by the pulse generator at frequencies between 10 and 20 Hz. Wave forms became more sinusoidal as pulse frequency decreased to 5 Hz. Wave forms over 20 Hz tended to be spiked. The difference between maximum and minimum pressures decreased as frequency increased. Some stretching of the vest or expansion of the connecting tubing was observed at the maximum pressure portion of the pulse indicated by a slight drop in pressure after initial pressure rise. The pressure rise time was generally about twice as fast as the decay time at frequencies of 10 Hz or above. The pressure rise time for the near square wave 173 was at least twice as fast as a sine wave 175 having equivalent amplitude and frequency would be (compare y to x). The pressure rise time is a function of the rotary valve port shape and size and the constant pressure generated by the regenerative blower. Venting, however, is a function of forces in the system and the pressure in the patient vest which is decreasing constantly over the venting phase.

Figure 5:
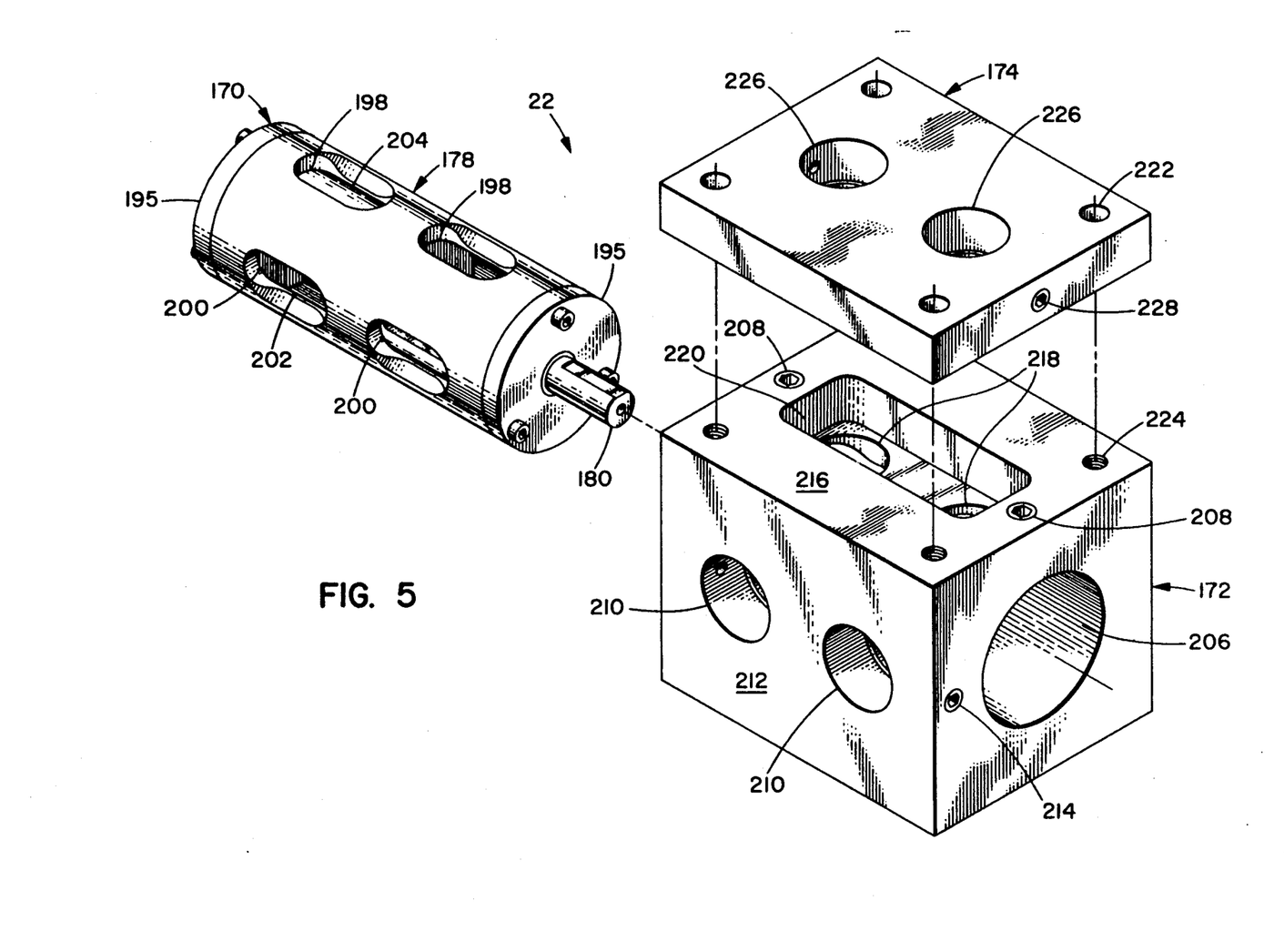
FIG. 5 is an exploded perspective of a rotary valve in accordance with the present invention.
Figure 6:
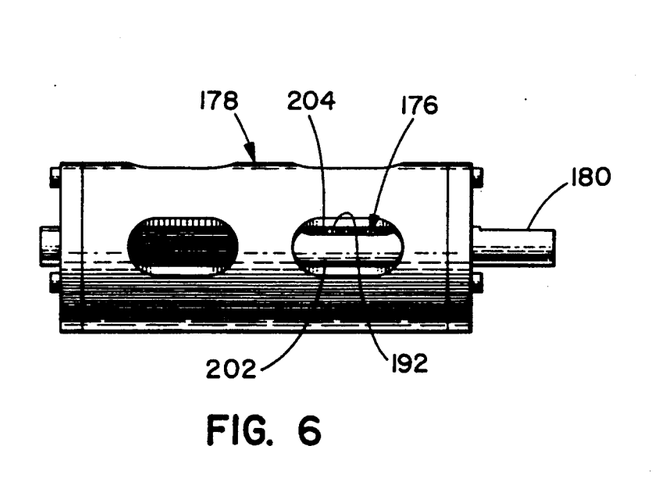
FIG. 6 is a side view of the rotor assembly for the valve of FIG. 5.
Figure 7:
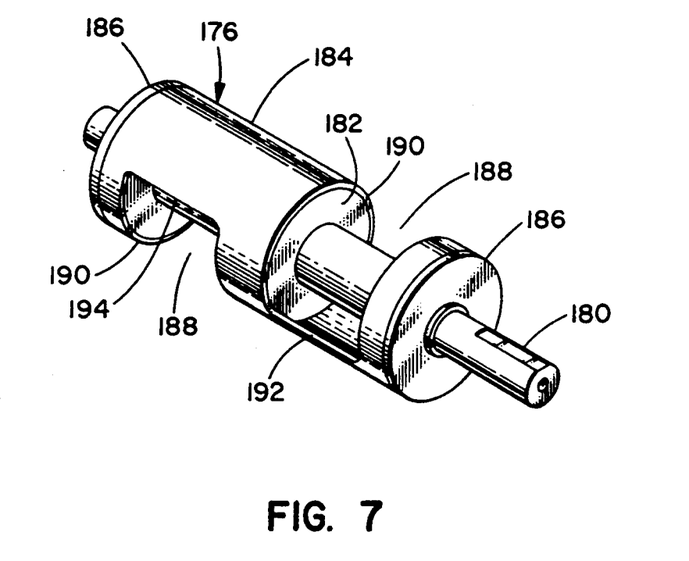
FIG. 7 is a perspective view of the rotor for the assembly of FIG. 6.

Rotary valve 22 representative of a type which can create substantially square wave pulses acceptable for solving the present problem related to chest therapy is shown in FIGS. 5-7. Rotary valve 22, described now in detail, includes a rotor assembly 170, which fits in housing 172. Housing 172 includes a cover 174 for forming a mixing chamber for preferably a pair of hoses connecting to vest 16. Rotor assembly 170 includes a rotor 176 (see FIGS. 6 and 7) in a close sliding relationship with bushing 178. Rotor 176 includes a shaft 180 passing therethrough. A separation wall 182 is mounted centrally on shaft 180, and a cylindrical shutter 184 is fixed to separation wall 182. Cover plates 186 formed in the shape of rings are fastened at opposite ends of shutter 184 and also fit on shaft 180. Openings 188 are cut in shutter 184 on each side of separation wall 182. Openings 188 have side edges 190 perpendicular to shaft 180 and have leading and trailing edges 192, 194 parallel with shaft 180. The intersections of the various edges may be rounded.

As shown in FIGS. 5 and 6, rotor 176 fits within bushing 178. Bearings (not shown) are fitted on shaft 180 against each cover plate 186 at the opposite ends of rotor 176. Cover plates 195 fastened to bushing 178 hold the bearings in place. Bushing 178 extends at each end beyond covers 186 of rotor 176 to provide space to receive the bearings.

Bushing 178 has two pair of elongated openings 198, 200. Each pair is elongated along a centerline (not shown) which is parallel with shaft 180. The centerlines of the two pairs of openings are separated by 90° relative to the axis of shaft 180. Each opening 198, 200 has forward-most and rearward-most edges 202 and 204 which are straight and parallel with shaft 180. At a slight distance outwardly from the innermost portion of edges 202, 204, the edges are beveled so as to further open openings 198, 200 and decrease any resistance to flow. The ends of openings 198, 200 may be semi-cylindrical.

As shown in FIG. 6, the interrelationship of the leading and trailing edges 192, 194 of rotor 176 with the forward-most and rearward-most edges 202, 204 of bushing 178 allow the registration of the openings to open and close as elongated slits thereby creating very rapid surges of pressurized air or closures of same. In particular, as a straight rearward-most edge of a bushing passes a straight trailing edge of a shutter, an elongated opening quickly expands and passes pressurized air in the form of a pulse approaching a square wave. Square wave pulses as created by rotary valve 22 and illustrated in FIG. 8 can be contrasted with registrations of circular openings (not shown) which lead to pulses having much slower rise times and which approach sine wave rise times. It is noted that square wave pulses can be created with other designs as well, e.g., a linear shuttle valve.

Rotor assembly 170 fits into housing 172 as shown in FIG. 5. Housing 172 has a central, cylindrical passage 206 for receiving rotor assembly 170. Set screws 208 are tightened against bushing 178 to fix it from rotating. Consequently, with shaft 180 fastened in a conventional fashion to a motor 53, rotor 176 is free to turn and function appropriately. A pair of openings 210 are formed in one of the rectangular walls 212 of housing 172. Openings 210 are aligned with openings 200 of rotor assembly 170. Tubes (not shown) are fitted against a flange at the inner end of openings 210 and are held in place by set screws 214. At a wall 216 adjacent to wall 212, another set of openings 218 are formed. Openings 218 are aligned with openings 198 in rotor assembly 170. A cavity 220 extends between openings 218 in the external face of wall 216 and in combination with cover plate 174, forms a plenum chamber to provide interchange of air flow from vest 16 to rotor 176 on either side of separation wall 182. Cover plate 174 is fastened to wall 216 with screws (not shown) at openings 222, 224 in a conventional way. Cover plate 174 includes a pair of openings 226 for receiving tubes (not shown) which connect with vest 16. The tubes (not shown) are held in place with set screws 228.

The portion of shutter 184 which extends between leading and trailing edges 192 and 194 is greater than a 90° portion of the cylindrical surface. The edges on the opposite sides of separation wall 182 are related such that when a trailing edge 194 passes a forward-most edge 202 on one side of separation wall 182, a leading edge 192 passes a rearward-most edge 204 on the other side. In this way, air flow to and from vest 16 is always in fluid communication with either blower 26 or atmosphere, but never both.

With rotary valve 22 operating as described, pressures at various locations inside the inflatable vest 16 were measured. All measurements were done on large (4,000 sq. cm) and small (2,000 sq. cm) vests while being worn by a patient. With atmospheric venting the highest maximum pressure of 39 mm Hg was measured in the front upper ⅓ of the vest at pulse frequency of 25 Hz.

These were also the conditions under which the highest minimum pressure of 29 mm Hg was measured. The lowest maximum pressure was 26 mm Hg and was measured at the most distal portion (lower ⅓ of back) from input port and lowest pulse frequency of 5 Hz. These were also the conditions under which the lowest minimum pressure of 8 mm Hg was measured. With atmospheric venting both the maximum and minimum curves were concave upwards and the difference decreased with increase in pulse frequency. At 4 Hz the maximum pressure was 39 mm Hg and minimum was 26 mm Hg. With vacuum assisted venting the maximum and minimum pressure curves are linear and the difference was constant from 5 to 25 Hz.

Pressures throughout the vest 16 were consistent at each frequency. The greatest maximum pressure difference at any frequency from the input port to the most distal portion of the vest was 2 mm Hg. The greatest minimum pressure difference at any frequency from the input port to the distal portion of the vest was 4 mm Hg. Vest size or tightness of fit had little effect on pressure, maximum or minimum, at pulse frequencies of 5 to 25 Hz.

The difference between maximum and minimum pressures was consistent throughout the vest. The greatest difference was 4 mm Hg at 10, 20, and 25 Hz. The smallest was 2 mm Hg at 5 Hz.

The venting time of the vest to background pressure of 5 mm Hg was less than one second regardless of vest size and fit. This pressure is low enough so that inspiration is not impaired. This slight residual pressure is desirable to keep the vest inflated between breathing cycles so that maximum pulse pressures are attained in a few pulse cycles.

Comparison of mucus (sputum) production using conventional chest physical therapy and the invention was done on 5 cystic fibrosis patients at the University of Minnesota Hospital. Thirty therapy sessions used the invention at 12–16 Hz and thirty sessions used standard chest physical therapy done by a certified respiratory therapist. Time of day of the therapy was matched and total volume of mucus produced after each session was recorded. All therapy sessions were of equal duration.

Early clinical observations indicate efficacy in increased mucus (sputum) production and in improved lung function. The mean mucus production for conventional therapy sessions was 1.8 cc and for therapy sessions with the invention was 3.3 cc. The standard error of the means was 0.39 and 0.54, respectively. A two-sided t test of the paired therapies showed a statistically significant difference (P value<0.001) between the two methods with the invention producing more mucus.

Clinical efficacy has been quantified in a vest user using the invention who is not participating in clinical trials, i.e., a 48 year-old male with cystic fibrosis with *Pseudomonas aeruginosa* in his sputum and with a two-year overall worsening of his pulmonary function who, after a year of use of the vest with the invention, had improved pulmonary function to the level of five years earlier. Furthermore, the technesium aerosol scan before vest therapy with the invention showed absence of ventilation in the upper lobes with restoration of ventilation in these areas after 8 months of use of the vest with the invention.

Our early pressure pulse generators used variable speed pistons, metal bellows and neoprene air spring bellows as described hereinafter. Each of these configurations had drawbacks. They produced only the less desirable sinusoidal pulse wave forms and required auxiliary source of air to reinflate the vest between patient breathing cycles. The volume of air required to inflate a large vest also made it necessary to have large displacement pistons or bellows. The noise, weight, power requirements, difficult volume control, and less effective pulse wave form made those systems undesirable.

Pressure pulse wave form of the present system is a function of the shape and size of the rotary valve ports and the pressure applied to the valve. The quick dump design of the valve ports allows for maximum opening in a short time. A constant 130 mm Hg pressure air stream is applied to the valve during the pulsing phase. The air stream is chopped into pulses and directed to the inflated vest. The quick dump action of the valve allows such a sharp initial pressure rise that some pressurization stretching of the vest and tubing is observed. The pressure fall side of the pulse is determined by the pressure in the vest and the shape and size of the valve ports. The vent port is not open long enough to vent the vest to the pressures obtained at the lower frequencies. Since the minimum pressure is higher at higher frequencies, the maximum pulse pressure is also increased. A vacuum assist of 10 mm Hg was applied to the vent side of the system in early designs. It caused reduction in pressure change and lowered maximum pulse pressure. A drawback of the vacuum assist was an increased vest reinflation time from less than half a second to 3–4 seconds. Patient preference was uniformly for the atmospheric venting system.

Inflation and deflation curves of the vest controlled by the patient were constant regardless of frequency. This allows the patient to inhale without difficulty. Short reinflation time is important as it allows effective pulsing immediately after maximum inhalation by patient.

At any frequency the pressures inside the vest varied little (4 mm Hg) from the input port to the distal portion of the vest, providing effective therapy since the entire torso is pulsed at nearly the same pressure.

Even though vest size or snugness of fit had slight effect on pressure, we feel fit is an important consideration. The vest should fit tight enough for minimal inflation time. This allows the inside wall of the vest expansion room to push against the patient. Early models of the vest had a non-stretchable exterior and a stretchable inner wall. Under these conditions, areas along the margin of the vest ballooned and reduced the pulse strength. For this reason, a non-stretchable inner wall is used.

To summarize, preliminary observations show the preferred embodiment just discussed to be more effective than standard chest physical therapy, with a statistically significant increase in mucus production and evidence of improved pulmonary function.

To complete our disclosure, an early embodiment of apparatus 10 referenced above is depicted in FIG. 1. Apparatus 10' is shown schematically in FIG. 3. The pulse pumping system comprises a pair of bellows 88 and 90 which may be air ride springs of a type commonly used for suspension of large vehicles. Bellows 88 and 90 operate in opposite directions. Bellows 88 and 90 are driven by a one-half horsepower DC electric motor 93 connected by a five millimeter timing belt 112 to a centrally mounted crankshaft 96. The timing belt runs in conjunction with a pair of pulleys 108 and 110. The crankshaft is held in position by bearing pillow blocks 98 and 100. A DC variable speed motor controller 142 is used to regulate motor speed.

Figure 3:
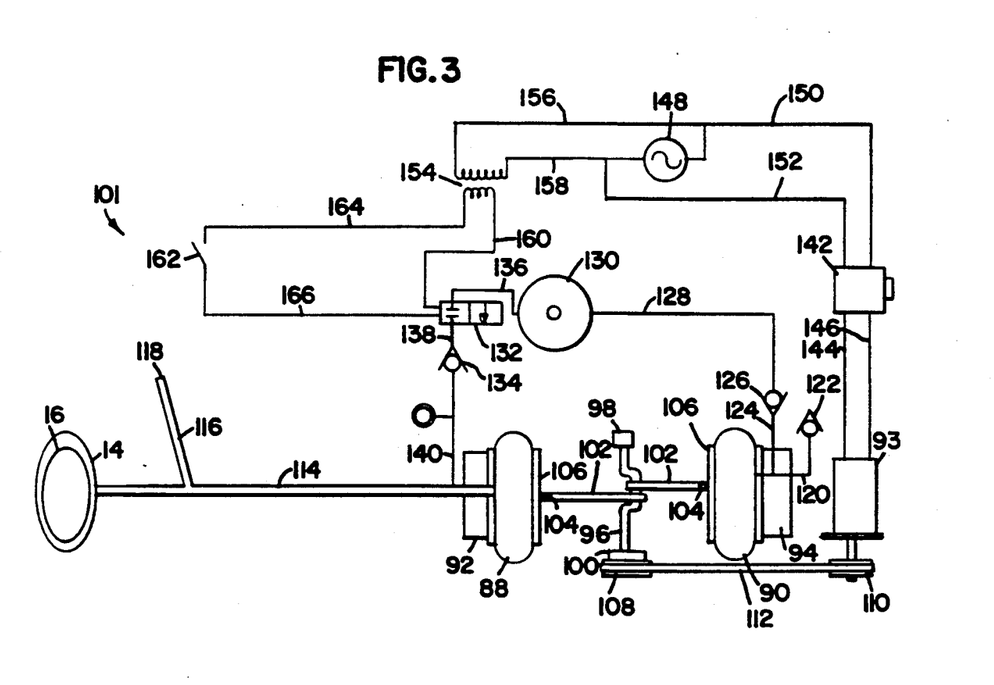
FIG. 3 is a schematic diagram of an apparatus in accordance with the alternate embodiment illustrated in FIG. 1.

The primary bellows 88 is in direct fluid communication with the vest bladder 16 on the patient. Air is compressed in and evacuated out of the vest by the primary bellows at a rate of typically 10 to 30 hertz. The volume of the pulse is calibrated to patient size and is dependent on the length of the pump stroke and the diameter of the bellows.

The secondary bellows 90 provides an additional airflow to vest bladder 16 which allows the patient to regulate vest bladder contact pressure. This has importance since little or no pressure is needed or in fact desired while the chest wall is expanding during inspiration as previously discussed. Therefore, during inspiration air in the vest bladder is vented to atmosphere, and after inspiration a rapid reinstatement of pressure is necessary for effective chest compression before the next breathing cycle begins. The secondary bellows 90 has directional air flow through a series of one way valves to a small air storage tank 130. The pressure of the air storage tank builds to about on psi during patient inspiration, while the air vest bladder 16 vents to atmosphere. The patient regulates the pressure of the vest bladder by covering or uncovering a vent hole on air hose 116 with a finger. When the vent is open, air is vented to atmosphere. When the patient closes the vent hole and also closes switch 162 controlling solenoid valve 132, the compressed air in the air tank is dumped into the inflatable vest bladder. Such action provides quick reinflation of the vest after the patient has finished inhaling to achieve a contact pressure which is efficient for effective oscillatory chest compression.

More particularly, apparatus 10' as shown in FIG. 3 includes primary bellows 88 and secondary bellows 90, both of which are driven by DC motor 93. On the sides facing away from one another, both primary and secondary bellows 88 and 90 are held by identical base members 92 and 94. Each base member 92 and 94 presents a flat solid surface against which the bellows 88 and 90 may be compressed. Crank shaft 96 is supported by bearing pillow blocks 98 and 100. Connecting rods 102 are appropriately attached to crank shaft 96 at one end and at an opposite end may be attached through a universal joint 104 to a plunger 106. It is understood that the present description relates only to functional components and that structural framework is necessary and may be easily envisioned and constructed by one skilled in the art. Pulleys 108 and 110 fasten to crank shaft 96 and the shaft of motor 93, respectively, to support timing belt 112.

Primary bellows 88 is in fluid communication through tube 114 with vest bladder 16. Tube 114 includes a branch tube 116 with an open end 118 which the patient closes when he/she wants pressure in vest bladder 16 and opens when he/she wants to vent vest bladder 16. Secondary bellows 90 receives make up air through tube 120 having a one way check valve 122 open in a flow direction leading toward secondary bellows 90. Secondary bellows 90 is also in fluid communication through tube 124 with one way check valve 126 leading in a flow direction away from secondary bellows 90. Valve 126 is in fluid communication through tube 128 with air storage tank 130. Air storage tank 130 is in fluid communication with tube 114 through solenoid valve 132 and one way valve 134 providing flow only in a direction away from storage tank 130, via tubes 136, 138 and 140. When solenoid valve 132 is open, air from storage tank 130 flows to either or both primary bellows 88 and vest bladder 16. In particular, make up air for primary bellows 88 is supplied by vest bladder 16 or storage tank 130.

Motor 93 is electrically connected with controller 142 via lines 144 and 146. Controller 142 is connected to power source 148 via lines 150 and 152. Solenoid valve 132 is isolated from power source 148 by transformer 154. The primary side of transformer 154 is connected to source 148 via lines 156 and 158. The secondary side of transformer 154 is connected to solenoid valve 132 via line 160 and through patient controlled switch 162 via lines 164 and 166.

To use, as with embodiment 10, firstly the vest bladder and shell 16 and 14 are fitted on patient 12. The patient places one had at the end of tube 116 and the other hand holds switch 162. Motor 93 is started and regulated to a desired speed in a fashion as described with respect to the preferred embodiment apparatus 10' using motor controller 142. The patient must then learn when to apply compression relative to his/her breathing cycle. That is, during expiration, the patient opens switch 162 and closes end 118 of tube 116. During inspiration, it is generally desirable to vent vest bladder 16 so that the patient then opens switch 162 and opens end 118 of tube 116.

Thus, although the embodiments disclosed provide pressure pulses to the thoracic region of a patient and allow the patient to control the rate of the pulses and the application of the pulses, it is apparent that the actual components of various systems are different. In this regard, it is understood then that even though the advantages and details of structure and function of the embodiments have been set forth, they are nevertheless exemplary and other equivalents are possible. Therefore, changes made, especially in matters of shape, size and arrangement to the full extent extended by the general meaning of the terms in which the appended claims are expressed, are within the principle of the present invention.

What is claimed is:

1. Compression apparatus for thoracic region of a person, comprising:

means for applying a force to the thoracic region of said person, said force applying means including a bladder for receiving pressurized air;

means for supplying pressure pulses of said pressurized air to said bladder, said pulses having a rise time at least twice as fast as the rise time of a sinusoidal pulse of equivalent amplitude and frequency; and means for venting said pressurized air from said bladder.

2. Compression apparatus for thoracic region of a person, comprising:

means for applying a force to the thoracic cavity of said person, said force applying means including a bladder for receiving pressurized air;

means for creating a stream of pressurized air;

means for communicating said stream from said creating means to said bladder, said communicating means including means for forming a pressure pulse, said pulse forming means including a valve having a port with an opening with a straight rearward-most edge, said valve further having a shutter with a straight trailing edge which is substantially parallel with said straight rearward-most edge of said port opening wherein a pulse approaching a square wave is created as said shutter edge passes said opening edge to expose said bladder to said air pressure creating means; and means for venting said pressurized air from said bladder.

3. Apparatus in accordance with claim 2 wherein said pulse forming means includes means for changing frequency.

4. Apparatus in accordance with claim 2 including means for interrupting flow of said air stream from said creating means to said pulse forming means.

* * * * *